United States Patent [19]
Kikuchi

[11] Patent Number: 5,921,974
[45] Date of Patent: Jul. 13, 1999

[54] DISPOSABLE DIAPER WITH SHAPED ABSORBENT MEMBER

[75] Inventor: Fumiaki Kikuchi, Iwate-ken, Japan

[73] Assignee: Kao Corporation, Tokyo, Japan

[21] Appl. No.: 08/894,131

[22] PCT Filed: Dec. 24, 1996

[86] PCT No.: PCT/JP96/03767

§ 371 Date: Aug. 13, 1997

§ 102(e) Date: Aug. 13, 1997

[87] PCT Pub. No.: WO97/24091

PCT Pub. Date: Jul. 10, 1997

[30] Foreign Application Priority Data

Dec. 28, 1995 [JP] Japan .................................. 7-342663

[51] Int. Cl.$^6$ .................................................. A61F 13/15
[52] U.S. Cl. .................. 604/385.1; 604/358; 604/385.2; 604/392
[58] Field of Search ................................. 604/358, 378, 604/385.1, 385.2, 386, 387, 392, 393, 396, 401, 402; 128/885, 891

[56] References Cited

U.S. PATENT DOCUMENTS

| | | | |
|---|---|---|---|
| 780,598 | 1/1905 | Coleman et al. | 604/401 |
| 1,928,330 | 9/1933 | Dewitt | 604/401 |
| 3,400,718 | 9/1968 | Saijo . | |
| 4,019,517 | 4/1977 | Glassman | 604/401 |
| 4,327,732 | 5/1982 | Thinnes | 604/385.1 |
| 4,589,876 | 5/1986 | Van Tilburg | 604/385.1 |
| 4,900,319 | 2/1990 | Richwine | 604/385.1 |
| 4,917,697 | 4/1990 | Osborn et al. | 604/387 |
| 4,964,858 | 10/1990 | Livny | 604/385.1 |
| 5,449,353 | 9/1995 | Watanabe et al. | 604/385.2 |
| 5,792,130 | 8/1998 | Widland et al. | 604/385.1 |

FOREIGN PATENT DOCUMENTS

| | | | |
|---|---|---|---|
| 0622063 | 11/1994 | European Pat. Off. . | |
| 663072 | 3/1994 | Japan . | |
| 6114084 | 4/1994 | Japan . | |
| 9516418 | 6/1995 | WIPO | 604/385.1 |

*Primary Examiner*—Mark O. Polutta
*Attorney, Agent, or Firm*—Birch, Stewart, Kolasch & Birch, LLP

[57] ABSTRACT

A disposable diaper includes a front body and a back body. The front and back bodies each has a liquid permeable topsheet, a liquid impermeable topsheet, a liquid impermeable backsheet and a liquid retentive absorbent element interposed between the topsheet and the backsheet. The front and back bodies each include a body covering portion and a pair of leg covering portions extending downwardly from the body covering portion, wherein the absorbent element of the front body and the absorbent element of the back body are continuous at the crotch portion of the diaper to form a unitary absorbent member. The absorbent member has a pair of wing portions extending laterally from opposite longitudinal the edges of the absorbent member. The wing portions are made to bend downwardly at the crotch portion of the diaper in such a manner that the wing portions are brought into contact with the inner crotch portion of a wearer when the diaper is in a wearing state.

17 Claims, 5 Drawing Sheets

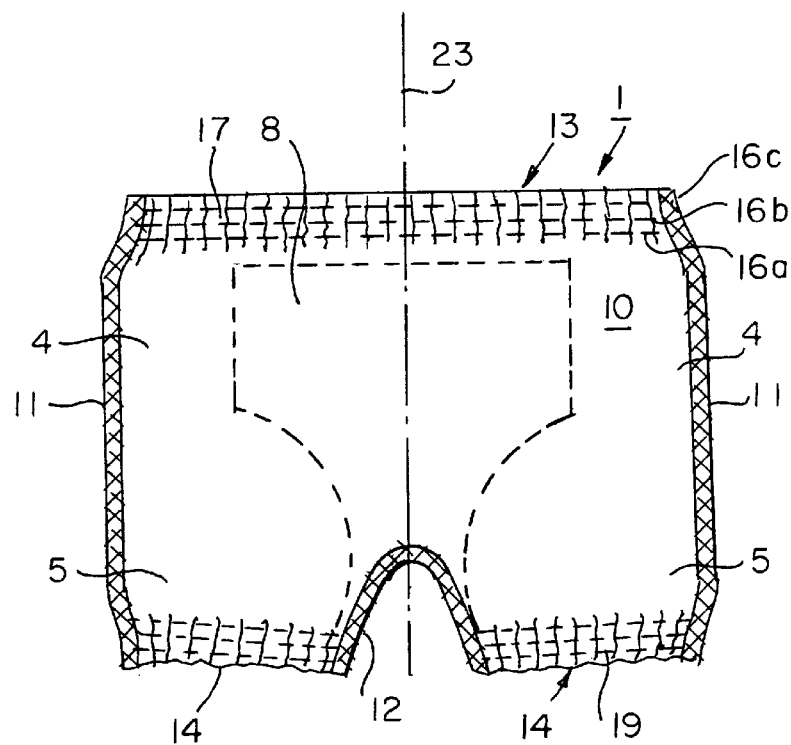
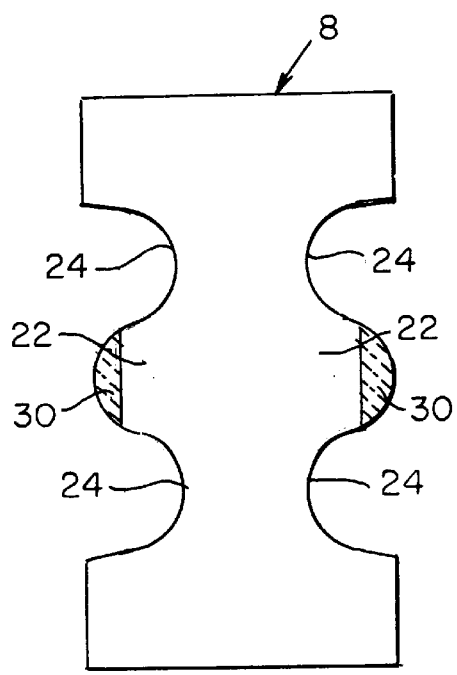
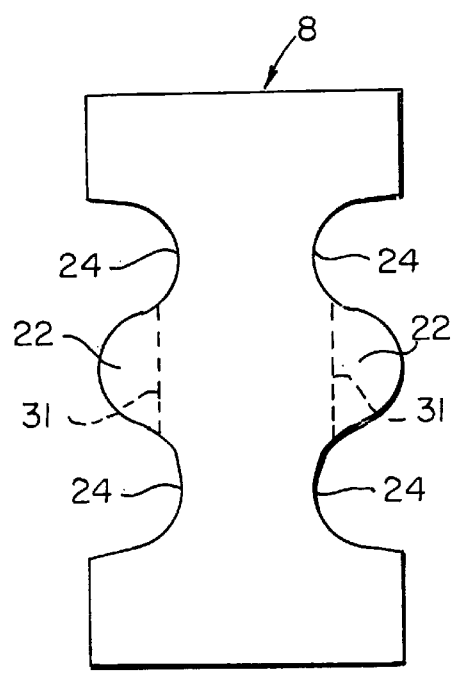

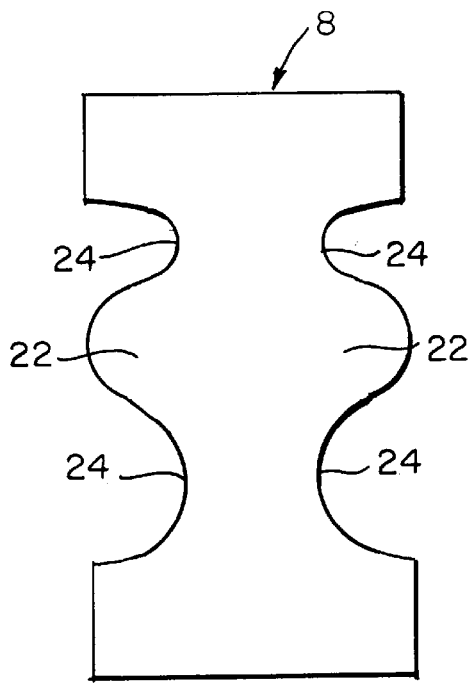
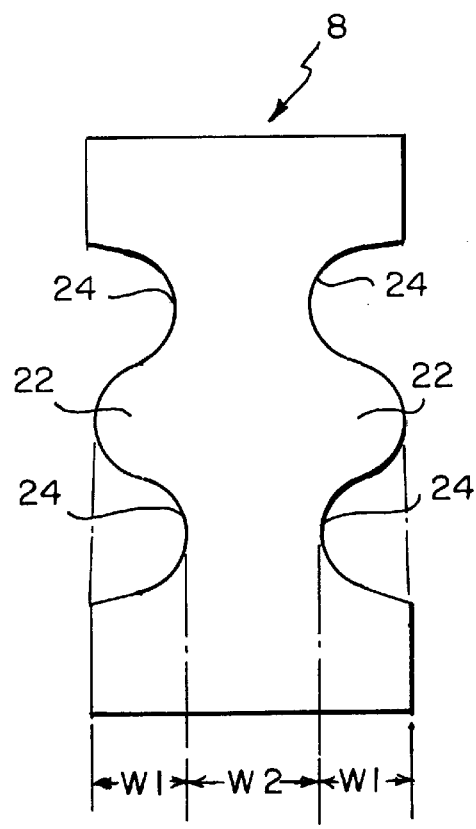
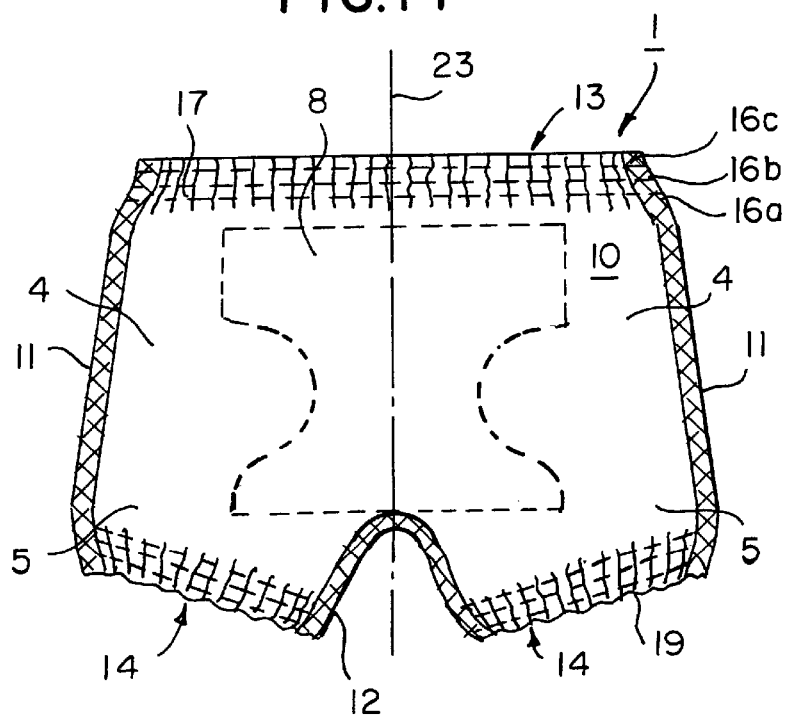

DISPOSABLE DIAPER WITH SHAPED ABSORBENT MEMBER

TECHNICAL FIELD

This invention relates to a disposable diaper, and more particularly to a disposable diaper capable of providing a comfortable feel of wear at the crotch portion and having a large liquid absorption capacity.

BACKGROUND ART

As disposable diapers for infants, incontinent persons and the like, shorts type diapers and flat type (development type) diapers have heretofore been used. Since each of these diapers has a thick absorbent member which is provided over the entire longitudinal area of the diaper including the crotch portion thereof, the absorbent member becomes bulky and many wrinkles are formed at the crotch portion of the diaper when the diaper is being worn. The result is that the comfort during wear is unfavorably degraded.

It can be contemplated as a means for improving the feel of wear of the diaper that, for example, the width at the crotch portion of the diaper is decreased to reduce the quantity of the absorbent member existing at the crotch portion. However, since the discharge of liquid is mostly concentrated at the crotch portion, this means is liable to degrade the liquid absorption, thereby causing liquid leakage from the crotch portion.

On the other hand, as means for realizing both the comfort during wear and large liquid absorption capacity at the crotch portion, disposable diapers as disclosed, for example, in Japanese Laid-Open Patent Applications 6-114084 and 6-63072, etc. are known.

However, in the disposable diaper of Japanese Laid-Open Patent Application 6-114084, the front and back bodies are separately made and therefore, the absorbent member is cut into a front body and a back body at the crotch portion. The result is that liquid is liable to leak from the crotch portion.

On the other hand, in the disposable diaper of Japanese Laid-Open Patent Application 6-63072, an auxiliary pad is provided on a discontinuous portion of the absorbent member at the crotch portion in order to prevent the leakage of liquid from the crotch portion. However, since the absorbent member is thick, the feel of wear cannot be improved.

It is, therefore, an object of the present invention to provide a disposable diaper which is comfortable during wear at the crotch portion and is improves in preventing liquid leakage from the crotch portion.

DISCLOSURE OF THE INVENTION

As a result of intensive study, the inventors of the present invention have found out that the above goal can be achieved by employing a so-called trunks-type configuration as a configuration of a diaper having a front body and a back body each comprising a body covering portion and a pair of leg covering portions and by making the absorbent member into a specific configuration at the crotch portion.

The present invention has been accomplished based on the above findings and achieved the above goal by providing a disposable diaper comprising a front body and a back body, the front and back bodies each having a liquid permeable topsheet, a liquid impermeable backsheet and a liquid retentive absorbent element interposed between the topsheet and the backsheet, the front and back bodies each comprising a body covering portion and a pair of leg covering portions extending downwardly from the body covering portion, wherein said absorbent element of said front body and said absorbent element of said back body are continuous at the crotch portion of said diaper to form a unitary absorbent member, said absorbent member having a pair of wing portions extending laterally from opposite longitudinal side edges of said absorbent member, said wing portions being made to bend downwardly at the crotch portion of said diaper in such a manner that said wing portions are brought into contact with the inner crotch portion of a wearer when said diaper is in a wearing state.

Also, the present invention provides a disposable diaper having a liquid impermeable backsheet and a liquid retentive absorbent member wherein said backsheet comprises a body covering portion and a pair of leg covering portions extending downwardly from said body covering portion, and said absorbent member having a pair of wing portions extending laterally from opposite longitudinal side edges of said absorbent member and is releasably adhered to the crotch portion of said backsheet.

BRIEF DESCRIPTION OF THE DRAWINGS

FIG. 9 is a front view showing another preferred embodiment of a disposable diaper according to the present invention (corresponding to FIG. 1);

FIG. 10 is a plan view of an absorbent member used in another preferred embodiment of the disposable diaper of the present invention (corresponding to FIG. 3);

FIG. 11 is a plan view of an absorbent member used in another preferred embodiment of the disposable diaper of the present invention (corresponding to FIG. 3);

FIG. 12 is a plan view of an absorbent member used in another preferred embodiment of the disposable diaper of the present invention (corresponding to FIG. 3);

FIG. 13 is a plan view of an absorbent member used in another preferred embodiment of the disposable diaper of the present invention (corresponding to FIG. 3); and FIG. 14 is a front view showing another preferred embodiment of a disposable diaper according to the present invention (corresponding to FIG. 1).

DETAILED DESCRIPTION OF THE INVENTION

A preferred embodiment of a disposable diaper according to the present invention will now be described with reference to the accompanying drawings. Here, FIG. 1 is a front view showing a preferred embodiment of a disposable diaper according to the present invention, and FIG. 2 is a sectional view taken on line A—A of the disposable diaper shown in FIG. 1.

Figure 1:
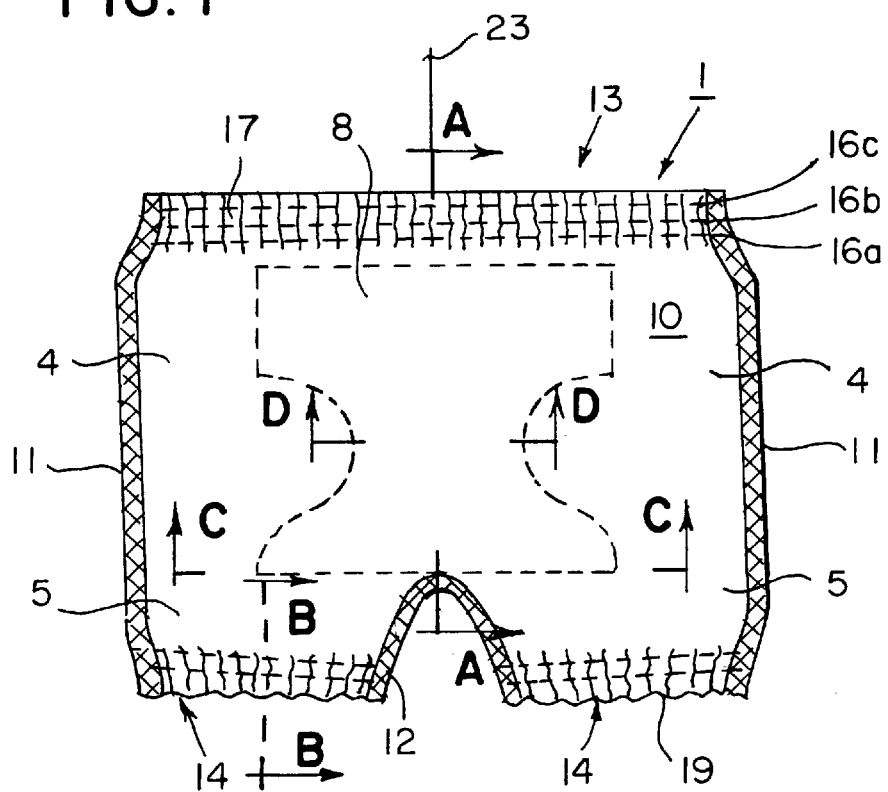
FIG. 1 is a front view showing a preferred embodiment of a disposable diaper according to the present invention.
Figure 2:
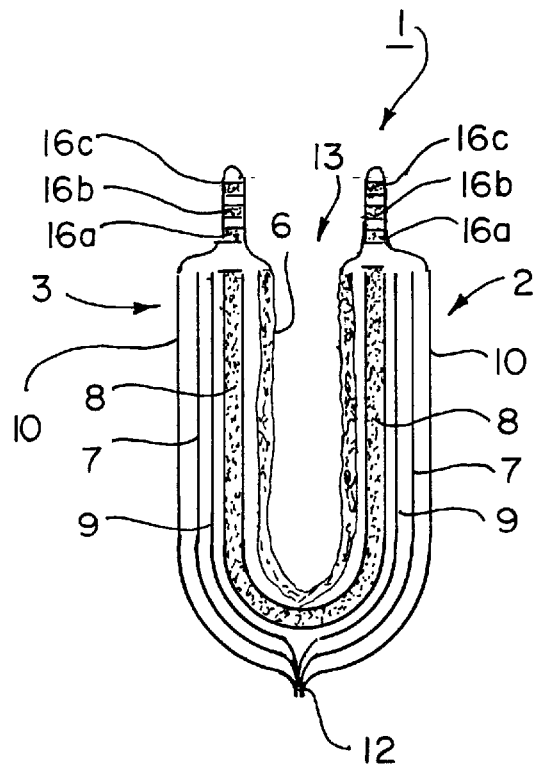
FIG. 2 is a sectional view taken on line A—A of the disposable diaper shown in FIG. 1.

The disposable diaper 1 shown in FIGS. 1 and 2 includes a front body and a back body 3. Each of the front and back bodies 2 and 3 comprises a body covering portion 4 and a pair of leg covering portions 5, 5 extending downwardly from the body covering portion 4. Thus, this disposable diaper 1 has a so-called trunks-type configuration.

As shown in FIG. 2, each of the front and back bodies 2 and 3 has a liquid permeable topsheet 6, a liquid impermeable backsheet 7 and an absorbent element 8 interposed between the topsheet 6 and the backsheet 7. The topsheet 6 is located on an inner side of the diaper 1 so as to come in direct contact with the skin of a wearer. On the other hand, the backsheet 7 is located on an outer side, i.e., skin non-contacting side (that side which does not contact the skin of a wearer), of the diaper 1.

As shown in FIGS. 1 and 2, in the disposable diaper 1 of this embodiment, side cover sheets 9, 9 are arranged inwardly of the backsheets 7 in the front and back bodies 2 and 3, and outer covers 10, 10 are arranged outwardly of the backsheets 7 in the front and back bodies 2 and 3. The side cover sheets 9, 9 are arranged such that they contact directly the skin of a wearer at that area other than the area where the topsheet 6 covers the absorbent element. A top surface of the disposable diaper 1 is constituted by the outer covers 10, 10. As shown in FIG. 1, the backsheets 7, 7, the side cover sheets 9, 9 and the outer covers 10, 10 are joined together at opposite side edges 11, 11 and at the crotch portion 12 by suitable joining means such as heat sealing or the like, so that a waist opening portion 13 and a pair of leg opening portions 14, 14 are formed. In addition, the backsheet 7, the side cover sheet 9 and the outer cover 10 are fixedly joined together by such joining means as a hot melt adhesive or the like.

As shown in FIGS. 1 and 2, in the disposable diaper 1 of this embodiment, an upper end portion of the outer cover 10 is folded back towards the topsheet 6 side at the waist opening portion 13. At the folded-back portion, three elastically expansible members 16a, 16b, 16c are provided in their expanded states around the waist opening portion 13, thereby forming a waist gather 17. In this embodiment, the elastically expansible members 16a, 16b, 16c are gradually increased in their degree of expansion towards an opening end of the waist opening portion 13. That is, the waist gather 17 is gradually reduced towards the opening end of the waist opening portion 13. As a consequence, the waist opening portion 13 has a funnel-like configuration towards the opening end. Since the waist opening portion 13 has such a special configuration, the disposable diaper 1 can further enhance the fitness of the diaper at the waist opening portion 13 so that urine and feces are effectively prevented from leaking through the waist opening portion 13, while the disposable diaper 1 can maintain a comfortable feel during wear as a whole due to the relaxed fitness which is derived by a trunks-like configuration. The degree of expansion of the elastically expansible members 16a, 16b and 16c are, in general, preferably from 120 to 280% at the elastically expansible member 16a which is most remotely located from the opening end and from 140 to 300% and from 160 to 320% respectively at the elastically expansible members 16b, 16c which are located near the opening end, although the degree of expansion depends, as a matter of course, on materials and configurations of the elastically expansible members to be employed.

Figure 4:
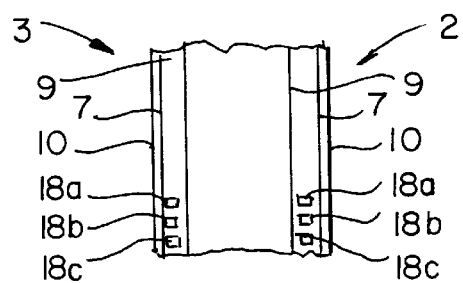
FIG. 4 is a sectional view taken on line B—B of the disposable diaper shown in FIG. 1.

Further, in the disposable diaper 1 of this embodiment, as shown in FIG. 1 and FIG. 4 (FIG. 4 is a sectional view taken on line B—B of FIG. 1), three elastically expansible members 18a, 18b and 18c are provided in their expanded states between the backsheet 7 and the side cover sheet 9 at each of the leg opening portions 14, 14, thereby forming a pair of leg gathers 19, 19, respectively. In this embodiment, the elastically expansible members 18a, 18b and 18c are gradually decreased in their degree of expansion towards the opening end of each leg opening portion 14. That is, each leg gather 19 is gradually reduced towards the opening end of the leg opening portion 14. As a consequence, the leg opening portion 14 has, as in the waist opening portion 13, a funnel-like configuration towards the opening end. Since the leg opening portion 14 has such a special construction, the diaper 1 can effectively prevent urine and feces from leaking through the leg opening portion 14, while the disposable diaper 1 can maintain a comfortable feel during wear as a whole due to the relaxed fitness which is derived by a trunks-like configuration. The degree of expansion of the elastically expansible members 18a, 18b and 18c are, in general, preferably from 120 to 250% at the elastically expansible member 16a which is most remotely located from the opening end and from 130 to 260% and from 140 to 270% respectively at the elastically expansible members 18b, 18c which are located near the opening end, although the degree of expansion depends, as a manner of course, on materials and configurations of the elastically expansible members to be employed.

Figure 3:
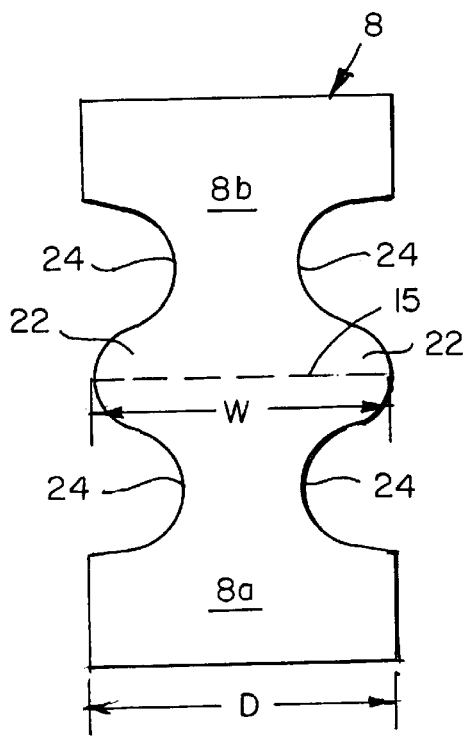
FIG. 3 is a plan view of an absorbent member which can be used in the disposable diaper shown in FIG. 1.

Next, the absorbent elements 8a and 8b which make up the absorbent member 8 of the disposable diaper according to this embodiment will be described with reference to FIG. 3. The absorbent element 8a of the front body 2 and the absorbent element 8b of the back body 3 have narrowed portions 24, 24, respectively, each exhibiting a so-called sandglass-like configuration. The absorbent element 8a of the front body and the absorbent element 8b of the back body are integrally connected together at the crotch portion of the diaper to form a unitary absorbent member 8. That is, the absorbent element 8a of the front body and the absorbent element 8b of the back body are continuous at the crotch portion of the diaper 1. The absorbent member 8 can be folded along a folding line 15 of FIG. 3 towards the body side of a wearer. As shown in FIG. 3, the width of the absorbent member 8 at the crotch portion is larger than the width of the area located between the body portion and the crotch portion, namely, the width of the most-narrowed portion 24. That is, the absorbent member 8 has at the crotch portion a pair of wing portions 22, 22 extending laterally from opposite longitudinal side edges of the absorbent member, respectively. The distance W between the tips of the wing portions 22, 22 in the absorbent member 8 is generally equal to the width D at the body portion.

Next, an internal construction of the disposable diaper 1 according to this embodiment will be described with reference to FIGS. 5 and 6. Here, FIG. 5 is a sectional view taken on line C—C of FIG. 1, and FIG. 6 is a sectional view taken on line D—D of FIG. 1.

Figure 5:
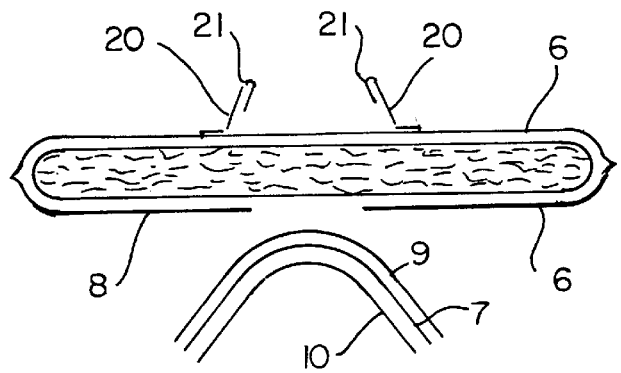
FIG. 5 is a sectional view taken on line C—C of the disposable diaper shown in FIG. 1.
Figure 6:
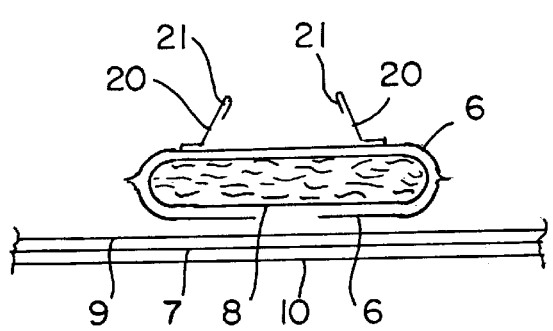
FIG. 6 is a sectional view taken on line D—D of the disposable diaper shown in FIG. 1.

As shown in FIGS. 5 and 6, the disposable diaper 1 according to this embodiment is designed such that the liquid permeable topsheet 6 is provided on that side (skin contacting side) of the absorbent member 8 which contacts the skin of a wearer in such a way so as to enclose the absorbent member 8. The side cover sheet 9, the liquid impermeable backsheet 7 and the outer cover 10 are provided on the skin non-contacting side. The topsheet 6 is cut into the configuration of the absorbent member 8. Each of the topsheets 6, 6 are joined together at the side portions of the absorbent member 8 by such joining means as a hot melt adhesive, heat sealing or the like. The absorbent member 8 which is enclosed by the topsheet 6 and the side cover sheet 9 are fixedly joined together by a hot melt adhesive or the like, except for the wing portions 22, 22.

As shown in FIGS. 5 and 6, a pair of erected gathers 20, 20 which are connected to the topsheet 6 are formed on opposite longitudinal side portions of the absorbent member 8. Each erected gather is fixedly joined, at one longitudinal side edge thereof, to the topsheet 6 and is free at another side edge thereof. The free end of the erected gather is folded back towards the longitudinal center axis of the absorbent member 8. Elastically expansible members 21, 21 are fixedly provided in their expanded states at the folded-back portion. Also, as shown in FIG. 6, the erected gathers 20, 20 are provided such that they are located inwardly of the most-narrowed portion of the absorbent member 8. As shown in FIGS. 5 and 6, the erected gathers 20, 20 are collapsed inwardly, and are erected when the diaper is in a wearing state. As a consequence, since the erected gathers 20, 20 function as liquid leakage preventive walls and improve the receiving characteristics of discharged materials, liquid leakage through the crotch portion caused by movement of a wearer can more effectively be prevented.

Next, the liquid absorbing action, which is exhibited by the disposable diaper according to this embodiment, will be described with reference to FIGS. 7 and 8. Here, FIG. 7 is a perspective see-through view showing a state of the absorbent member before the disposable diaper according to this embodiment is in a wearing state, and FIG. 8 is a perspective see-through view showing a state of the absorbent member wherein the disposable diaper according to this embodiment is in a wearing state.

As previously described, in the disposable diaper 1 according to this embodiment, the absorbent element 8a of the front body 2 and the absorbent element 8b of the back body 3 are continuous at the crotch portion of the diaper to form the unitary absorbent member 8. In addition, the absorbent member 8 is made to be wider at the crotch portion of the diaper thereby forming the pair of the wing portions 22, 22. Accordingly, in the disposable diaper 1 according to this embodiment, as shown in FIG. 7, the absorbent member 8 at the crotch portion, i.e., the wing portions 22, 22; are extended towards the leg opening portions 14, 14 before the diaper is brought into a wearing state.

Figure 7:
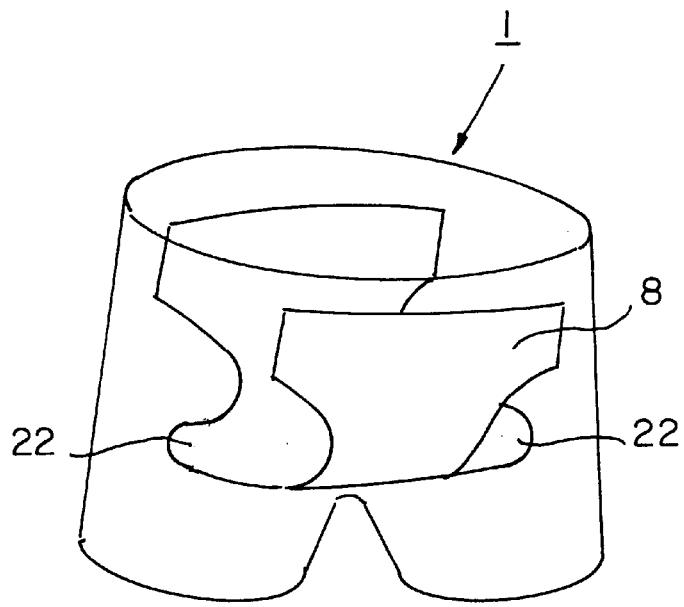
FIG. 7 is a perspective see-through view showing a state of the absorbent member before the disposable diaper according to this embodiment is in a wearing state.
Figure 8:
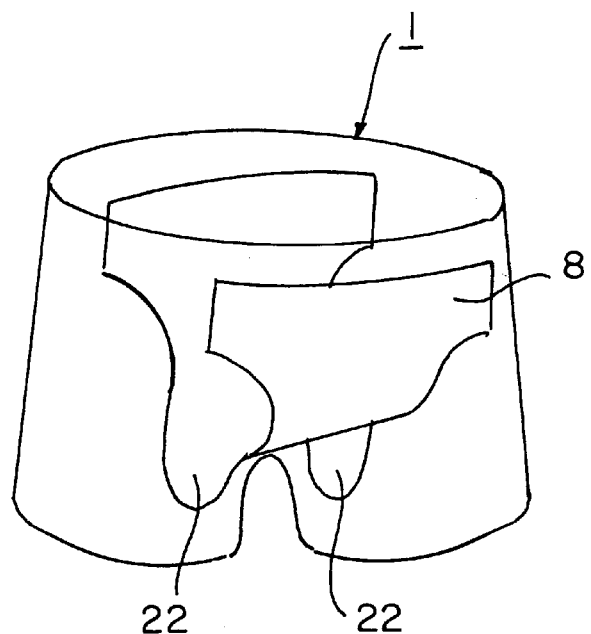
FIG. 8 is a perspective see-through view showing a state of the absorbent member wherein the disposable diaper according to this embodiment is in a wearing state.

When the disposable diaper 1 shown in FIG. 7 is in a wearing state, the wing portions 22, 22, as shown in FIG. 8, are made to bend downwardly along the direction of insertion of the legs of a wearer and the erected gathers 20, 20 (not shown) stand more erect. As a consequence, the wing portions 22, 22 are brought into contact with the inner crotch of a wearer through the outer cover 10, the backsheet 7 and the side cover sheet 9. Accordingly, discharged liquid is usually absorbed by an absorption area defined by the pair of erected gathers 20,20. Even if some discharged liquid, which could not have been absorbed by the absorption area, should leak over the erected gathers, such discharged liquid would be securely absorbed by the wing portions 22, 22. Thus, liquid leakage through the crotch portion can be prevented very effectively.

Next, materials of various members used in the disposable diaper according to this embodiment will be described. The material of the liquid permeable topsheet 6 is not particularly limited as long as it has such properties as being able to permeate the discharged material into the absorbent member 8. It is particularly preferred that the material of the liquid permeable topsheet 6 is selected from those having the feel of undergarments. Preferred examples of such liquid permeable sheets include woven fabrics, non-woven fabrics such as carded or spunbonded fabrics or perforated films made of thermoplastic resins. In order to enhance the liquid permeability of the topsheet, a hydrophilic compound such as alkyl phosphate ester may be applied to the surface of the topsheet.

A preferred material of the liquid impermeable backsheet 7 includes a film sheet obtained by adding a filler of an inorganic or organic compound to a thermoplastic resin, melt-extruding the resulting mixture through a T-die or a circular die, and then, subjecting the extrudate to monoaxial or biaxial orientation; and a film sheet having moisture permeable and liquid impermeable properties obtained by molding a thermoplastic elastomer through the melt-extrusion method or the solvent casting method. It is also preferred that the backsheet 7 is elastically expansible. An example of such a liquid impermeable sheet includes a composite material composed of a thermoplastic resin film or non-woven fabric and a thermoplastic resin film, or the like.

An acceptable material of the liquid retentive absorbent member includes a fluff pulp obtained by pulverizing a wood pulp. It is preferred that such a fluff pulp is used in combination with a superabsorbent polymer. It is particularly preferred to use a heat-treated mixture of a thermoplastic resin, a fluff pulp and a superabsorbent polymer. The superabsorbent polymer may be mixed to a fluff pulp, or alternatively the superabsorbent polymer may present in a particular portion, i.e., upper layer portion, intermediate layer portion or lower layer portion, of the absorbent member 8. It is preferred that the superabsorbent polymer has an absorption capacity of absorbing and retaining a liquid twenty times or more the dead weight and is in a particle form in which the superabsorbent polymer can be readily gelled. Examples of such superabsorbent polymers include starches, celluloses and synthetic polymers, and in particular, starch-acrylic acid (or salt thereof) graft copolymer, saponified starch-acrylonitrile copolymer, cross-linked sodium carboxymethyl cellulose and acrylic (or salt thereof) polymer.

It is preferred that the materials of the outer cover sheet 10 and the side cover sheet 9 are selected from those having the feel of undergarments and having moisture permeablity. Preferred examples of such sheets include woven fabrics, composite materials of a thermoplastic resin film and non-woven fabric, and the like.

The erected gather 20 preferably has hydrophobic properties from a leakage preventing view point. Preferred examples include non-woven fabrics, thermoplastic films, composite materials of a thermoplastic resin film and a non-woven fabric, and the like.

Acceptable materials of the elastically expansible members 16, 18, 21 constituting the waist gather 17, the leg gather 19 and the erected gather 20 are polyurethane or natural rubber of a string or a strip form. In particular, rubber of a string form, strip form or film form, or foamed polyurethane of a film form, etc. are preferred. In this case, materials of the elastically expansible members constituting the waist gather 17, the leg gather 19 and the erected gather 20 may be the same or different.

Next, other embodiments of the present invention will be described hereinbelow.

According to another preferred embodiment of the present invention, as shown in FIG. 9, the wing portions 22, 22 are pre-bent and pre-fixed to the leg opening portions 14, 14 of the disposable diaper 1 before the disposable diaper 1 is in a wearing state. The disposable diaper of this embodiment is advantageous in that liquid is more effectively absorbed since the wing portion 22, 22 are hardly shifted from their normal position even when the wearer moves violently.

According to another preferred embodiment of the present invention, as shown in FIG. 10, the wing portions 22, 22 have water-repellent portions 30, 30 at the tips of the wing portions, in particular, at the side of the skin-noncontacting surface of the wing portions. The disposable diaper of this embodiment is advantageous in that the leakage of liquid absorbed by the wing portions 22, 22 is more effectively prevented. The water-repellent portions 30, 30 are made water-repellent, for example, by a water-repellent agent, or by joining a water-repellent sheet to the tips of the wing portions.

According to another preferred embodiment of the present invention, the wing portions 22, 22 are made to be easily bent downwardly. For example, as shown in FIG. 11, bending portions 31, 31 of the wing portions 22, 22 are made thinner than the other portions of the wing portions 22, 22, or alternatively, the bending portions 31, 31 of the wing portions 22, 22 have a notch.

According to still another preferred embodiment of the present invention, as shown in FIG. 12, the wing portions 22, 22 are offset forward or backward from the longitudinal center of the absorbent member 8, thereby the wing portions 22, 22 more suitably fit to the body of a wearer.

According to still another preferred embodiment of the present invention, as shown in FIG. 13, the width of each of the wing portions $W_1$, is narrower than that of the crotch portions $W_2$ of the disposable diaper, thereby the wing portions 22, 22 are brought into contact with the inner crotch portion of a wearer at a suitable contacting area.

According to yet another preferred embodiment of the present invention, the width of each of the wing portions does not extend beyond the leg opening portions 14, 14 or the leg gathers 19, 19 provided at the leg opening portions when the wing portions 22, 22 are bent downwardly, thereby leakage of liquid is more effectively prevented.

According to yet another preferred embodiment of the present invention, the disposable diaper has a liquid impermeable backsheet and a liquid retentive absorbent member. The backsheet comprises a body covering portion and a pair of leg covering portions extending downwardly from the body covering portions. The absorbent member has a pair of wing portions extending laterally from opposite longitudinal side edges of the absorbent member, and is releasably adhered to a crotch portion of the backsheet.

Having been described preferred embodiments of the disposable diaper according to the present invention, it should be noted, however, that the disposable diaper according to the present invention is not limited to the above embodiments, and many changes and modifications can be made.

For example, the distance W between tips of the wing portions in the absorbent member may be different from the width D at the body portion of the absorbent member. In other words, the relation may be W >D or W <D depending on liquid absorption capacity, etc.

Also, the opposite side edges 11 of the disposable diaper 1, may be generally in parallel relation with respect to the longitudinal center axis 23 of the disposable diaper 1 as shown in FIG. 1, or alternatively, they may diverge (i.e., go away from the center axis 23) towards the leg opening portion as shown in FIG. 14.

Also, the erected gather may extend from the topsheet or from the backsheet.

INDUSTRIAL APPLICABILITY

As described in detail above, according to the disposable diaper of the present invention, a trunks-type configuration is employed as a configuration of the diaper, the absorbent member is continuous at the crotch portion, and the wing portions are formed at the crotch portion. Accordingly, an excellent feel of wear at the crotch portion can be obtained, and the effect of leakage prevention from the crotch portion is enhanced.

Also, the waist gather or the leg gathers are preferably formed around the waist opening portion or the leg opening portions, and the opening area of the waist opening portion or the leg opening portion is preferably reduced toward the opening end. Accordingly, the disposable diaper of the present invention can further enhance the fitness of the diaper at the waist opening potion or the leg opening portions so that urine and feces are effectively prevented from leaking through the waist opening portion or the leg opening portions, while the disposable diaper can maintain the comfortable feel of wear as a whole due to the relaxed fitness which is derived by a trunks-like configuration.

Also, the backsheet of the diaper is preferably elastically expansible. Accordingly, the disposable diaper fits well to a wearer even if the wearer moves busily. In addition, a soft holding feel can be given to the whole diaper, and leakage of urine and feces can be prevented more effectively.

I claims:

1. A disposable diaper comprising.
   a front body; and
   a back body, the front and back bodies each having a liquid permeable topsheet, a liquid impermeable backsheet and a liquid retentive absorbent element interposed between the topsheet and the backsheet, the front and back bodies each including a body covering portion and a pair of leg covering portions extending downwardly from the body covering portion, the absorbent element of the front body and the absorbent element of the back body are continuous at the crotch portion of the diaper to form a unitary absorbent member, said absorbent member including opposite longitudinal edges, the absorbent member having narrow portions and a pair of wing portions extending laterally from the opposite longitudinal edges of the absorbent member said wing portions define a first width dimension which is substantially greater than a second width dimension defined by said narrow portions, the wing portions being made to bend downwardly at the crotch portion of the diaper in such a manner that the wing portions are brought into contact with the inner crotch portion of a wearer when the diaper is in a wearing state.

2. The disposable diaper according to claim 1, wherein the wing portions are pre-bent and pre-fixed to leg opening portions of the diaper before the diaper is in a wearing state.

3. The disposable diaper according to claim 1, wherein the wing portions have water-repellent portions at the tips thereof.

4. The disposable diaper according to claim 3, wherein the water-repellent portions are made water-repellent by a water-repellent agent.

5. The disposable diaper according to claim 3, wherein the water-repellent portions are made water-repellent by joining a water-repellent sheet to the tips of the the wing portions.

6. The disposable diaper according to claim 1, wherein bending portions of the wing portions are made thinner than other potions of the wing portions.

7. The disposable diaper according to claim 1, wherein the bending portions of the wing portions have a notch.

8. The disposable diaper according to claim 1, wherein the wing portions are offset forward or backward from the longitudinal center of the absorbent member.

9. The disposable diaper according to claim 1, wherein the width of each of the wing portions W1 is narrower than that of the crotch portion of the diaper.

10. The disposable diaper according to claim 1, wherein the width of each of the wing portions does not extend beyond the leg opening portions or leg gathers provided at the leg opening portions when the wing portions are bent downwardly.

11. The disposable diaper according to claim 1, wherein elastically expansible members are provided around the leg opening portions, thereby forming the leg gathers.

12. The disposable diaper according to claim 11, wherein the leg gathers are gradually reduced towards opening ends of the leg opening portions.

13. The disposable diaper according to claim 1, wherein an elastically expansible member is provided around a waist opening portion of the diaper, thereby forming a waist gather.

14. The disposable diaper according to claim 13, wherein the waist gather is gradually reduced towards the opening end of the waist opening portion.

15. The disposable diaper according to claim 1, wherein a pair of erected gathers which are connected to the topsheet are formed on opposite longitudinal portions of the absorbent member.

16. The disposable diaper according to claim 1, wherein the backsheet is elastically expansible.

17. A disposable diaper comprising:

a front body; and a back body, the front and back bodies each having a liquid permeable topsheet, a liquid impermeable backsheet and a liquid retentive absorbent element interposed between the topsheet and the backsheet, the front and back bodies each including a body covering portion and a pair of leg covering portions extending downwardly from the body covering portion, the absorbent element of the front body and the absorbent element of the back body are continuous at the crotch portion of the diaper to form a unitary absorbent member, said absorbent member including opposite longitudinal edges, the absorbent member having a pair of wing portions extending laterally from the opposite longitudinal edges of the absorbent member, said absorbent member including at least one pair of narrow portions disposed adjacent to said wing portions, the wing portions being made to bend downwardly at the crotch portion of the diaper in such a manner that the wing portions are brought into contact with the inner crotch portion of a wearer when the diaper is in a wearing state.

* * * * *